United States Patent [19]

Petit et al.

[11] Patent Number: 5,843,887
[45] Date of Patent: Dec. 1, 1998

[54] COMPOSITIONS FOR DELIVERY OF POLYPEPTIDES, AND METHODS

[75] Inventors: Serge Petit, Aubenas; Emile Bourland, deceased, late of Persan, both of France, by Jacqueline Bourland, legal representative

[73] Assignee: Allied Medical Research Associates, Washington, D.C.

[21] Appl. No.: 951,308

[22] Filed: Oct. 16, 1997

Related U.S. Application Data

[63] Continuation of Ser. No. 412,347, Mar. 31, 1995, abandoned.

[30] Foreign Application Priority Data

Sep. 1, 1994 [FR] France .................................. 94 10673

[51] Int. Cl.⁶ .......................... A61K 38/28; A61K 38/00; C07K 5/00; C07K 1/00
[52] U.S. Cl. .................. 514/3; 514/12; 514/21; 530/303; 530/350; 530/412
[58] Field of Search .................. 514/3, 12, 21; 530/303, 350, 412

[56] References Cited

U.S. PATENT DOCUMENTS

| | | | |
|---|---|---|---|
| 4,279,886 | 7/1981 | Allen .................................. | 424/1 |
| 4,945,083 | 7/1990 | Jansen, Jr. .................................. | 514/52 |
| 5,227,311 | 7/1993 | Kuemmerle et al. ................... | 436/501 |
| 5,338,669 | 8/1994 | Gillies .................................. | 435/69.1 |
| 5,350,674 | 9/1994 | Boenisch et al. ..................... | 435/7.8 |
| 5,428,023 | 6/1995 | Russell-Jones et al. ................ | 514/21 |
| 5,449,720 | 9/1995 | Russell-Jones et al. ............... | 525/54.1 |

FOREIGN PATENT DOCUMENTS

| | | |
|---|---|---|
| 0220030 | 4/1987 | European Pat. Off. . |
| 0 595 005 | 5/1994 | European Pat. Off. . |
| 0 595 006 | 5/1994 | European Pat. Off. . |
| WO 92/17167 | 10/1992 | WIPO . |
| WO 93/19660 | 10/1993 | WIPO . |
| WO 94/27613 | 12/1994 | WIPO . |
| WO 94/27641 | 12/1994 | WIPO . |

OTHER PUBLICATIONS

M. Saffran et al., "A New Approach to the Oral Administration of Insulin and other Peptide Drugs", *Science*. vol. 233, pp. 1081–1084 (Sep. 5, 1986).

D. Shah et al., "Transferrin Receptor Mediated Delivery of Insulin–Transferrin Conjugate in CACO–2 Cells", *Pharmaceutical Research*. vol. 11, No. 10, p. S–7 (Oct. 1994).

Batt, R.M. and Horadagoda, N.U., "Gastric and pancrestic intrinsic factor–mediated absorption of cobalamin in the dog," *Am. J. Physiol*. 257:G344–G349 (1989).

Davis et al., "Type 1 diatetes and latent pernicious anaemia," *Med. J. Australia 156*: 160–162 (1992).

Hewitt et al., "Human Gastric Intrinsic Factor: Characterization of cDNA and Genomic Clones and Localization to Human Chromsome 11," *Genomics 10*432–440 (1991).

Jespersen et al., "Neurophysiological Variables and Fibrinlysis in Insulin–Dependent Diabetes Treated with an Aldose Reductase Inhibitor or Placebo," *Haemostasis 16*:453–457 (1986).

Johnston et al., "Genomic Structure and Mapping of the Chromosomal Gene for Transcobalamin I (TCN 1): Comparison to Human Intrinsic Factor," *Genomics 12*(3):459–464 (1992).

Johnston et al., Errata for *Genomics 12*(3):459–464 (1992), *Genomics 14*:208 (1992).

Sigma Chemical Company, Catalog for Biochemicals, Organic Compounds for Research and Diagnostic Reagents, pp. 583 (1995).

*Primary Examiner*—Charles L. Patterson, Jr.
*Assistant Examiner*—Lisa J. Hobbs
*Attorney, Agent, or Firm*—Sterne Kessler, Goldstein & Fox P.L.L.C.

[57] ABSTRACT

Compositions comprising intrinsic factor (IF), and in particular, compositions comprising substantially pure intrinsic factor (IF) and a polypeptide wherein said composition is substantially free of R protein; a method of delivering a composition to the portal and/or lymphatic circulation system of a host; and a method of producing the above-described composition.

6 Claims, No Drawings

COMPOSITIONS FOR DELIVERY OF POLYPEPTIDES, AND METHODS

This application is a continuation of application Ser. No. 08/412,347, filed Mar. 31, 1995, now abandoned.

BACKGROUND OF THE INVENTION

1. Field of the Invention

The present invention relates, in general, to compositions comprising intrinsic factor (IF). In particular, the present invention relates to a composition comprising substantially pure intrinsic factor (IF) and a polypeptide, wherein preferably said composition is substantially free of R protein; a method of delivering a composition to the portal and/or lymphatic circulation system of a host; and a method of producing the above-described composition.

2. Related Art

Intrinsic Factor

Intrinsic Factor (IF), a glycoprotein with a molecular weight of 50 kDa, comprises 351 amino acids and approximately 15% carbohydrate. IF was discovered by Castle in 1929 (Castle, W. B., *Am. J. Med. Sci.* 178:748–764 (1929)), when he demonstrated that two substances were needed to correct pernicious anemia. One, which he called "extrinsic factor," which is present in meat (now known to be Vitamin B12) and the other, "intrinsic factor," as it is still known today, which is present in gastric juice. A human gastric intrinsic factor (IF) cDNA has been isolated and sequenced (Hewitt et al., *Genomics* 10:432–440 (1991)).

IF is secreted by the parietal cells of the stomach in humans, cats, guinea pigs, and monkeys, by the chief cells in rats and mice, and by duodenal and pyloric mucous cells in the hog. IF secretion is stimulated by histamine, pentagastrin, and cholinergic drugs and is inhibited by H2 receptor antagonists (but not omeprazole), prostaglandins, somatostatin, and epidermal growth factor. IF secretion appears to be independent of acid or enzyme secretion. (Bockus, *Gastroenterology* 2:948 (1995)).

R proteins are a family of immunologically related glycoproteins which bind cobalamin (vitamin B12) in vivo. R proteins have a molecular weight of 60 kDa and are named due to their more rapid migration than IF in an electrophoretic field. R proteins are found in saliva and gastric secretions as well as in breast milk and plasma. The R protein found in saliva and gastric juice has a higher affinity for cobalamin than for IF at both acidic and neutral pH values. After liberation from proteins in the stomach, cobalamin binds with R proteins. Acid and pepsin are required to liberate dietary cobalamin from its protein bond (Bockus, *Gastroenterology* 2:948 (1995)). Sequencing of cDNA and genomic DNA of Transcobalamin I (TCI), a member of the R protein family, has revealed structural similarities between R protein and IF (Johnston et al., *Genomics* 12:459–464 (1992)). TCI carries 70% of the cobalamin circulating in the body. TCI-cobalamin complexes are cleared slowly from plasma, primarily by hepatocytes, where TCI is digested and cobalamin is secreted in bile. When IF is purified, R proteins are a contaminant present in partially pure IF (Sigma Catalogue, 1995, p. 583).

The cobalamin—R protein complex along with excessive R protein and IF enters the second portion of the duodenum where pancreatic proteolytic enzymes degrade both bound and free R proteins, but not IF. At a pH of 8, in the presence of trypsin, IF has an affinity for cobalamin that is 150 times greater than that of R protein. Within 10 minutes, cobalamin is completely bound to IF. The cobalamin—IF complex is extremely stable over a wide range of pH (3 to 9) and is highly resistant to proteases.

Bile may also play a role in cobalamin absorption. Biliary diversion, as by a T tube, results in cobalamin malabsorption that is restored by the replacement of bile. Bile salts may enhance the binding of IF-cobalamin to the ileal receptor, but whether this is physiologically important is not known. (Bockus, *Gastroenterology* 2:948 (1995)).

In the small intestine, cobalamin is absorbed both passively and actively. Passive absorption is important only when pharmacologic doses of cyanocobalamin are administered, as in pernicious anemia. In such circumstances, only 1% of doses of 100 to 500 $\mu$g is absorbed. This process is neither pH nor calcium dependent (Bockus, *Gastroenterology* 2:948 (1995)).

Active absorption of cobalamin occurs in the ileum where specific high affinity receptors for the cobalamin-IF complex are located. The small numbers of receptors on each cell, 300 to 400/cell, or 1 for each microvillus, probably explains the limited absorption capacity humans have for cobalamin (1 to 2 $\mu$g/day). The IF-cobalamin receptor binds the IF portion of the complex, but not free IF or cobalamin, suggesting that IF has separate domains for binding cobalamin. Binding requires a pH greater than 5.4 and calcium and magnesium, but no energy (Bockus, *Gastroenterology* 2:948 (1995)).

After binding, there is a 3 to 4 hour delay before cobalamin appears in the circulation. It is not known whether cobalamin enters the cell independently of IF or whether the entire complex is taken up, and then cleaved by the enterocyte. Within the enterocyte, cobalamin is bound to transcobalamin II (TCII), a protein mediating its transport to tissues. TCII is a 347 residue polypeptide with high affinity for cobalamin; it is not an R protein, and is unrelated to the other R proteins, TCI and TCIII. It is synthesized in liver and possibly enterocytes as well (Bockus, *Gastroenterology* 2:948 (1995)).

Shortly after cobalamin-TCII complexes enter the circulation, they bind to tissue membrane receptors and undergo pinocytosis. The TCII is then proteolytically degraded in the lysosome, yielding free cobalamin. TCII deficiency is associated with life-threatening cobalamin deficiency. Although TCII is the carrier for newly absorbed cobalamin, it is not the plasma carrier for most cobalamin (Bockus, *Gastroenterology* 2:948 (1995)).

In summary, IF binds cobalamin in the duodenum. Once the cobalamin—R protein complex has been cleaved by pancreatic proteolytic enzymes (presumably including elastase), the new compound, IF—cobalamin, passes through the small bowel to the ileum where it is absorbed.

Insulin

Since the discovery of insulin in 1921, numerous advances have been made in the treatment of diabetes mellitus. Exciting work has been performed in developing new delivery systems for insulin, but these systems have been plagued by numerous problems.

In the normal nondiabetic individual, insulin is secreted into the portal circulation where the major portion of it is extracted by and acted on by the liver. Consequently, insulin levels in the systemic circulation remain low. When insulin is administered subcutaneously, it enters into the peripheral circulation, as opposed to the portal circulation. Even though approximately 50% of systemically administered insulin is normally cleared in its first pass through the liver, unphysiologically high system insulin levels persist. A large body of evidence has been accumulated which shows a strong correlation between systemic hyperinsulinemia and the development of atherosclerotic disease, both microvascular and macrovascular (Eschwege, E. et al., *Horm Metab Res* (suppl 15):14–16 (1985)). Thus, in view of the above, as well as the discomfort, inconvenience and variability of absorption when insulin is given subcutaneously, numerous other delivery systems have been explored.

The delivery of insulin via the nasal route has been studied since 1935 (Major, R. H., *J. Lab. Clin. Med.* 21:278–80 (1935)) with significant advances made in the 1980's when insulin was combined with surfactant materials to enhance absorption through the nasal mucosa (Moses, A. C. et al., *Diabetes* 32:1040–47 (1983)). Problems which have been encountered using this delivery system include a low fraction of absorption (10–20%) requiring the use of large amounts of insulin, an extremely rapid rate of absorption with an onset of action within 10 minutes, local symptoms, and the inability to use longer acting insulins.

Pulmonary administration of aerosolized insulin has received far less attention than nasal delivery systems. However, there are some inherent advantages, the greatest of which is the larger absorptive surface area in the lungs. As with nasal insulin, pulmonary administration of aerosolized insulin does not escape the inherent complications associated with systemic hyperinsulinemia.

Additionally, insulin has been administered through the eyes, rectally, and transdermally. Chiou et al., *Journal of Ocular Pharmacology* 5:81–91 (1989) have investigated the systemic delivery of insulin through the eyes using topical solutions of insulin in association with absorption promoters. Efforts to administer insulin via the rectal route using suppositories have yielded promising results in regards to metabolic control and avoiding hyperinsulinemia since absorption is via the portal circulation. The unavoidable issue remains patient acceptance. Transdermal delivery systems have been successfully used for a variety of pharmaceutical products for years. However, the only successful transdermal delivery of insulin has been through the use of iontophoresis, a process whereby an electrical current induces the migration of ionic substances.

An extensive amount of research has been done, exploring ways to administer insulin orally. Obvious advantages include the ease of administration, patient acceptance, and avoidance of hyperinsulinemic states, as absorption may be via the portal circulation. However, the most significant barrier to successful oral administration of insulin has been the degradation of insulin by proteolytic enzymes in the GI tract. Various methods to protect insulin from these proteolytic enzymes have been studied. Rogues, M. et al., *Diabetes* 41(4): 451–456 (1992) showed that insulin associated with nanocapsules of isobutylcyanoacrylate retained biological activity after oral administration. Gwinup, G. et al., *SO General Pharmacology* 22(2):243–246 (1991), showed that insulin, when administered orally in capsules composed of methacrylic acid copolymers, was protected from the action of enteric and pancreatic peptidases, and rises in plasma insulin concentrations were associated with a corresponding fall in the concentration of C-peptides. Saffran, M. et al., *Journal of Endocrinology* 131:267–278 (1991) used an approach whereby insulin was protected in a gelatin capsule coated with an azopolymer which resists digestive enzymes, but is degraded by bacterial action in the colon. Of interest in this study was the measurement of portal vein insulin levels as an index of intestinal absorption. The authors were also able to document that rising levels of portal vein insulin were closely followed by a decline in hepatic glucose production. A fall in serum glucose levels, however, required large doses of insulin.

Other investigators have studied oral insulin entrapped with liposomes, but with variable results. Mixtures of lipids, coadministration of surfactants, and other co-polymers have also been studied.

SUMMARY OF THE INVENTION

The invention provides a composition comprising substantially pure intrinsic factor (IF) and a polypeptide, wherein said composition is substantially free of R protein.

The invention further provides a pharmaceutical composition comprising substantially pure intrinsic factor (IF) non-covalently bound to a polypeptide.

The invention also provides a pharmaceutical composition comprising substantially pure intrinsic factor (IF) and insulin.

The invention also provides a method of delivering a composition to the portal and/or lymphatic circulation system of a host comprising:

administering to said host a pharmaceutical composition comprising:

a) substantially pure intrinsic factor (IF), and b) a polypeptide, preferably with a physiological acceptable carrier, diluent, excipient or adjuvant, wherein said composition is substantially free of R protein and wherein said composition enters the portal and/or lymphatic circulation system.

The invention further provides a method of producing the above-described composition comprising:

a) isolating intrinsic factor from an animal comprising the step of incubating said intrinsic factor with an enzyme which degrades R-protein and not intrinsic factor, until said composition is substantially free of R protein, and b) adding a polypeptide to said intrinsic factor.

Further objects and advantages of the present invention will be clear from the description that follows.

DETAILED DESCRIPTION OF THE PREFERRED EMBODIMENTS

The present invention relates to a composition comprising substantially pure intrinsic factor (IF) and a polypeptide, wherein said composition is substantially free of R protein.

The present invention further relates to a pharmaceutical composition comprising substantially pure intrinsic factor (IF) non-covalently bound to a polypeptide.

For purposes of clarity of disclosure, and not by way of limitation, the detailed description of the invention is divided into the following subsections:

I. Production of Substantially Pure IF From Animal Tissue

II. Production of Substantially Pure IF Via Recombinant Techniques

III. Polypeptides to be Combined with IF

A. Polypeptides Generally

B. Insulin Specifically

IV. Binding IF to the Polypeptide of Interest

V. Pharmaceutical Compositions and Methods of Delivery

I. Production of Substantially Pure IF From Animal Tissue

In one embodiment of the invention, IF is purified from a sample which naturally produces IF. Such samples include organs, tissues, cells, protein extracts, or biological fluids. Any eukaryotic organism can be used as a source for IF, as long as the source organism naturally contains IF. As used herein, "source organism" refers to the original organism from which IF is derived. IF is defined herein to include active fragments of IF defined herein as fragments capable of directing adsorption of the polypeptide of the invention into the ileum of an animal.

In one preferred embodiment, IF is isolated from pig intestine. More specifically, yellow mucous membrane from the pylorus cavity of pig intestine is crushed and added to water. The mixture is left to settle several hours (with intermitent stirring) and sodium carbonate is added (preferably, to about ph 9–10). The product is stirred (preferrably, 2 to 5 hours) and acidified (preferably, to about pH 3–4) with acid (preferably, hydrochloric acid) and incubated for about 3 to 4 hours. The product is then centrifuged to remove the muds. An ammonia solution is added (preferably up to pH 9) and the liquid is incubated (preferably, for about 2 hours) before centrifugation and acidification (preferably, to about pH 6)(preferably, with acetic acid). Mineral salts and molecules with molecular weight below about 10,000 are removed by ultra-filtration. The filtered liquid is then dehydrated, preferably by lyophilization. The compound may also be pressurized, using hot air, not to exceed 200° C.

The IF is treated with elastase, a pancreatic proteolytic enzyme, which breaks down R proteins. Other enzymes, including papain, can also be used to break down the R proteins. A pure form of IF can also be chemically synthesized using techniques known in the art. The protein sequence of IF is shown in Hewitt et al., *Genomics* 10:432–440 (1991).

Either prior to digestion of R proteins or subsequent thereto, one skilled in the art can readily follow known methods for isolating polypeptides in order to obtain IF free of natural contaminants. These include, but are not limited to: immunochromatography, size-exclusion chromatography, HPLC, ion-exchange chromatography, and immuno-affinity chromatography.

IF is substantially pure if it contains less than 2% R protein. Preferably, the IF composition will contain less than 1% R protein. Even more preferably, the IF composition will contain less than 0.1% R protein. Most preferably, the IF composition will not contain a detectable amount of R protein using SDS PAGE or HPLC techniques.

II. Production of Substantially Pure IF Via Recombinant Techniques

The intrinsic factor of the present invention may also be produced via recombinant techniques. Such techniques employ the use of a recombinant DNA molecule comprising, 5' to 3', a promoter effective to initiate transcription in a host cell operably linked to a nucleic acid molecule encoding Intrinsic Factor. A human gastric intrinsic factor (IF) cDNA has been isolated and sequenced (Hewitt et al., *Genomics* 10:432–440 (1991)). The recombinant DNA molecule preferably comprises a vector and the recombinant DNA molecule.

As used herein, a cell is said to be "altered to express a desired peptide" when the cell, through genetic manipulation, is made to produce a polypeptide which it normally does not produce or which the cell normally produces at low levels. One skilled in the art can readily adapt procedures for introducing and expressing either genomic, cDNA, or synthetic sequences of IF into either eukaryotic or prokaryotic cells.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the IF polypeptide. An operable linkage is a linkage in which the regulatory DNA sequences and the DNA sequence sought to be expressed are connected in such a way as to permit gene sequence expression. The precise nature of the regulatory regions needed for gene sequence expression can vary from organism to organism, but shall, in general, include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

The IF gene of the present invention (or a functional derivative thereof) may be expressed in either prokaryotic or eukaryotic cells. Prokaryotic hosts are, generally, the most efficient and convenient for the production of recombinant polypeptides and, therefore, are preferred for the expression of the IF gene.

Prokaryotes most frequently are represented by various strains of *E. coli*. However, other microbial strains can also be used, including other bacterial strains. In prokaryotic systems, plasmid vectors that contain replication sites and control sequences derived from a species compatible with the host can be used. Examples of suitable plasmid vectors include pBR322, pUC118, pUC119 and the like; suitable phage or bacteriophage vectors include $\lambda$gt10, $\lambda$gt11 and the like; and suitable virus vectors include pMAM-neo, pKRC and the like. Preferably, the selected vector of the present invention has the capacity to replicate in the selected host cell.

Recognized prokaryotic hosts include bacteria such as *E. coli*, Bacillus, Streptomyces, Pseudomonas, Salmonella, Serratia, and the like. However, under such conditions, the peptide will not be glycosylated. The prokaryotic host must be compatible with the replicon and control sequences in the expression plasmid.

Preferred eukaryotic hosts include, for example, yeast, fungi, insect cells, mammalian cells either in vivo, or in tissue culture. Preferred mammalian cells include HeLa cells, cells of fibroblast origin such as VERO or CHO-K1, or cells of lymphoid origin and their derivatives. Using insect cells as hosts, the Drosophila alcohol dehydrogenase promoter can be used. Rubin, *Science* 240:1453–1459 (1988). Alternatively, baculovirus vectors can be engineered to express large amounts of ALK-7 in insects cells (Jasny, *Science* 238:1653 (1987); Miller et al., In: *Genetic Engineering* (1986), Setlow, J. K., et al., eds., *Plenum*, Vol. 8, pp. 277–297).

A wide variety of transcriptional and translational regulatory sequences can be employed, depending upon the nature of the host. The transcriptional and translational regulatory signals can be derived from viral sources, such as adenovirus, bovine papilloma virus, simian virus, or the like, where the regulatory signals are associated with a particular gene sequence which has a high level of expression.

Expression of IF in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., *J. Mol. Appl. Gen.* 1:273–288 (1982)); the TK promoter of Herpes virus (McKnight, *Cell* 31:355–365 (1982)); the SV40 early promoter (Benoist et al., *Nature* (London) 290:304–310 (1981)); the yeast gal4 gene sequence promoter (Johnston et al., *Proc. Natl. Acad. Sci.* (USA) 79:6971–6975 (1982); Silver et al., *Proc. Natl. Acad. Sci.* (USA) 81:5951–5955 (1984)).

In a preferred embodiment, the introduced nucleic acid molecule will be incorporated into a plasmid or viral vector capable of autonomous replication in the recipient host. Any of a wide variety of vectors can be employed for this purpose. Factors of importance in selecting a particular plasmid or viral vector include: the ease with which recipient cells that contain the vector can be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. coli* (such as, for example, pBR322, ColE1, pSC101, pACYC 184, πVX. Such plasmids are, for example, disclosed by *Molecular Cloning: A Laboratory Manual*, second edition, edited by Sambrook, Fritsch, & Maniatis, Cold Spring Harbor Laboratory, 1989.

Once the vector or nucleic acid molecule containing the construct(s) has been prepared for expression, the DNA construct(s) can be introduced into an appropriate host cell by any of a variety of suitable means, i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene molecule(s) results in the production of IF. This can take place in the transformed cells as such, or following the induction of these cells to differentiate (for example, by administration of bromodeoxyuracil to neuroblastoma cells or the like).

III. Polypeptides to be Combined with IF

The polypeptide to be combined with IF comprises an antibody or other binding polypeptide, a hormone, an enzyme, a lymphokine, an antibacterial polypeptide (e.g., a cecropin), an antiviral polypeptide (e.g., interferon α), lectins, growth factors, cytokines, or physiologically active fragments thereof of these polypeptides. Any polypeptide which is desired to be transported to the portal and/or lymphatic system can be coadministered with IF. The polypeptide to be combined with IF is defined herein to include monomeric and multimeric proteins, as well as oligopeptides, such as dipeptides, tripeptides, etc.

A. Polypeptides Generally

Typical polypeptides for delivery according to the invention include active substances such as hormones and bioactive peptides (and analogues and derivatives thereof) such as vasopressin, vasopressin derivatives (desmopressin (*Folia Endocrinologica Japonica* 54(5):676–691 (1978))), oxytocin, insulin, testosterone, interferons (alpha, beta, and gamma), somatotrophin, somatostatin, erythropoietin, colony stimulating factors (G-CSF, GM-CSF, CSF), and inhibin. Also included are oral vaccines, such as subunit vaccines, comprising the pharmaceutical composition of the invention.

Further examples of active substances include polypeptides such as growth hormones, prolactin, adrenocorticotropic hormone (ACTH), melanocyte stimulating hormone (MSH), thyroid hormone releasing hormone (TRH), its salts, and derivatives thereof (U.S. Pat. Nos. 3,957,247 and 4,100, 152), thyroid stimulating hormone (TSH), luteinizing hormone (LH), folicle stimulating hormone (FSH), calcitonin, parathyroid hormone, glucagon, pentagastrin, secretin, pancreazymin, cholecystokinin, angiotensin, human placental lactogen, human chorionic gonadotropin (HCG), enkephalin, enkephalin derivatives (U.S. Pat. No. 4,277,394, European patent application Publication No. 31567), endorphin, kyotorphin, interleukins (I, II, and III), tuftsin, thymopoietin, thymosin, thymostimulin, thymic humoral factor (THF), serum thymic factor (STF), and its derivatives (U.S. Pat. No. 4,229,438) and other thymic factors [*Medicine in Progress* 125(10):835–843 (1983)], tumor necrosis factor (TNF), motilin, dinorphin, bombesin, neurotensin, cerulein, bradykinin, urokinase, streptokinase, asparaginase kallikrein, substance P analogue and antagonist, nerve growth factor, blood coagulation factors VIII and IX, lysozyme chloride, polymixin B, colistin, gramicidin, bacitracin, protein synthesis stimulating peptides (British patent No. 8232082), gastric inhibitory protein (GIP), vasoactive intestinal protein (VIP), platelet-derived growth factor (PDGF), growth hormone releasing factor (GRF, somatocrinin), bone morphogenetic protein (BMP), and epidermal growth factor (EGF).

Suitable molecules further include bacterial adhesins, viral adhesins, toxin binding subunits and lectins.

B. Insulin Specifically

In a preferred embodiment, the invention relates to a new composition, obtained by combining insulin with Intrinsic Factor, which allows new forms of insulin therapy. All forms of currently available insulin can be used. It is believed—without being bound thereby—that when combined with insulin, Intrinsic Factor protects insulin from the actions of proteolytic enzymes in the gastrointestinal tract. It is believed that the IF-insulin compound is absorbed in the distal small bowel and then goes to the liver via the portal circulation.

The invention thus allows a method of administering insulin orally which provides numerous advantages for patient acceptance and compliance. The invention may also prevent some of the complications associated with high insulin levels in the systemic circulation, seen when insulin is given in an injectable form.

To produce the insulin/Intrinsic Factor compound, the intrinsic factor is placed in a buffered medium. Insulin, which can be obtained from a variety of sources, is then added to this solution. By way of preferred example only, an effective amount of a complex composition may comprise from 0.1 to 10,000 International Units of insulin to 10,000 Units of IF. More preferably, an effective amount of a complex composition comprises from 1 to 100 International Units of insulin to 10,000 Units of IF. The resulting Intrinsic Factor/insulin compound is then dialyzed, and can then be preserved by several methods, including but not limited to lyophilization. The resulting compound may then be made into a liquid, solid or paste.

Studies described herein in mice, have shown conclusively, that when this Intrinsic Factor/insulin combination was administered orally, there was a fall in serum glucose. As expected, no change in serum glucose was noted when insulin alone was given orally.

In one preferred embodiment, the present invention provides a pharmaceutical composition comprising substantially pure intrinsic factor (IF) and insulin. The substantially pure IF need not be free of R protein. However, preferably, the IF is substantially pure if it contains less than 2% R protein. More preferably, the IF composition will contain less than 1% R protein. Even more preferably, the IF composition will contain less than 0.1% R protein. Most preferably, the IF composition will not contain a detectable amount of R protein using SDS PAGE or HPLC techniques. Preferably, the pharmaceutical composition comprises a physiological acceptable carrier, diluent, excipient or adjuvant. More preferably, the composition is an oral pharmaceutical composition.

IV. Binding IF to the Polypeptide of Interest

The preparation of the new composition preferably involves placing the IF and the polypeptide of interest in a buffered solution which allows the binding of the two substances in such a way that when taken, the intrinsic factor acts as a carrier for the polypeptide of interest to be transported to the portal and/or lymphatic system, protecting the polypeptide of interest and facilitating the release of this polypeptide in the organism where it can be used.

The intrinsic factor is preferably bound to said polypeptide either covalently or non-covalently.

The polypeptide may be linked covalently, directly or indirectly to the IF. Where a cross-linking agent is used, the cross-linking agent may contain a disulfide bond or be cleavable by acid, base or periodate. Examples of cross-linking agents include: N-(4-azidophenylthio)-phthalimide; 4,4'-dithiobisphenylazide; dithio-bis-(succinimidyl-propionate); dimethyl-3,3'-dithio-bis-propionimidate.2HCl; 3,3'-dithio-bis-(sulfosuccinimidyl-propionate); ethyl-(4-azidophenyl)-1,3'-dithiopropionate; sulfo-succinimidyl-2-(m-azido-o-nitrobenzamido)-ethyl-1,3'-dithiobutyrimidate.HCl; N-succinimidyl-(4-azido-phenyl)-1,3'-dithiopropionate; sulfo-succinimidyl-2-(p-azido-salicylamido)-ethyl-1,3'-dithiopropionate; N-succinimidyl-3-(2-pyridythio)propionate; sulfosuccinimidyl-(4-azidophenyldithio)-propionate; 2-iminothiolane; disuccinimidyl tartarate; bis-[2-(succinimidyloxycarbonyloxyl)-ethyl]-sulfone and carbodimides. A description of suitable carbodimides is provided in Khorana, H. G., *Chem. Rev.* 53:145–166 (1953).

V. Pharmaceutical Compositions and Methods of Delivery

In another embodiment, the composition is a pharmaceutical composition comprising a physiological acceptable carrier, diluent, excipient or adjuvant. The composition can be administered orally or systemically (preferably, intravenously, intraperitoneally, intramuscularly, or subcutaneously). Most preferably, the pharmaceutical composition is an oral pharmaceutical composition.

The complexes described herein may be formulated into pharmaceutical or veterinarily acceptable compositions utilizing carriers and/or excipients as are well known in the art. Compositions may be in the form of a capsule, tablet, slow-release dosage form, elixir, gel, paste, or any other suitable dosage form as is well known in the art. Preferably, an enterically coated dosage form is used.

Preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, antimicrobials, antioxidants, chelating agents, inert gases and the like. See, generally, *Remington's Pharmaceutical Science,* 18th Ed., Mack Eds.

The composition according to this invention is not limited to compositions containing only IF and a polypeptide. The compositions can contain additional active compounds, ie. tertiary or higher pharmaceutical compositions.

Complexes and compositions according to this invention may be administered to a human or animal subject in need of treatment. A therapeutically effective amount of a complex or combination according to this invention is that which provides treatment of a particular disease state, examples of which include diabetes (insulin), Vitamin $B_{12}$ deficiency ($B_{12}$), anemia (EPO), infertility and cryptorchism (gonadotropin), hypersecretory syndromes (somatostatin), neutropenia (GM-CSF and GCSF), hypotensive crises (angiotensin), hypoglycemia (glucagon), coronary thrombolysis (streptokinase), etc.

What constitutes an effective amount will depend upon the nature of the disease being treated, the consulting physician or veterinary surgeon judgment, and other factors such as the age, weight and/or sex of the subject. By way of example only, an effective amount of the composition according to the invention may comprise from one nanogram to 10 grams of the combination in accordance with the invention. Preferably, 5 to 500 mg of the combination by unit dosage is used. By way of preferred example only, an effective amount of a complex composition may comprise from 0.1 to 10,000 International Units of the above-described polypeptide to 10,000 Units of IF. More preferably, an effective amount of a complex composition comprises from 1 to 100 International Units to 10,000 Units of IF.

In one further embodiment, the present invention relates to a method of producing the above-described compositions comprising:

a) providing an IF (preferably, substantially free of R protein) and b) adding a polypeptide to said intrinsic factor.

More preferably, the method isolates intrinsic factor from an animal comprising the step of incubating said intrinsic factor with an enzyme (for example, elastase) which degrades R-protein and not intrinsic factor, until said composition is substantially free of R protein.

In one embodiment, the present invention relates to a method of delivering a composition to the portal and/or lymphatic circulation system of a host comprising: administering to said host the above-described IF/polypeptide composition wherein said composition enters the portal and/or lymphatic circulation system.

The present invention is described in further detail in the following non-limiting examples.

EXAMPLE 1

100 Kg of yellow mucous membrane from the pylorus cavity of the pig were crushed and then added to 200 liters of water. 1 to 10 g elastase (dosage of 20 Sacchar Units per mg) was added, and 3 g sodium hydroxide was added to achieve pH 8. The product was incubated 12 hours at 37° C. and then cooled to 20° C. Sodium carbonate was added (10 g per liter) and the product was incubated 3 hours. Phosphoric acid was then added to achieve pH 5. The product was incubated 12 hours and then centrifuged to remove the muds.

Ammonia solution was added up to achieve pH 9 and the liquid was incubated overnight before acidification up to pH 5 and centrifugation. Ammonium sulfate was added (400 g per liter), and the product was centrifuged the next day. Molecules with molecular weight below 10,000 were removed by ultrafiltration. The product was then dehydrated by lyophilization.

10 g IF (dosage of 300 Units per mg; one unit will bind one nanogram of vitamin B12) was added to 1 liter of 0.02M phosphate buffered solution and stirred up to 37° C. A solution of human biogenetic insulin (Novo Nordisk) was then mixed with the buffered solution with a ratio of up to 1 I.U. of Insulin per 1000 Units of IF. The solution (with a prefered pH of about 6) was stirred at a temperature of 37° C. for 24 hours. The product was then dialysed at 4° C. and dehydrated by lyophilization.

50 mg of IF and 4 I.U. of insulin were combined and injected into the sutured duodenal cavity of mice. (This prevents the compound from passing into the stomach.) Decreases in serum glucose were documented (stardard model Tracer 1103385—Boehringer), up until death, depending on the dose. Insulin alone, when injected into the sutured duodenal cavity, did not cause a fall in serum glucose.

EXAMPLE 2

0.08 I.U. of porcine insulin (AKZO) per mg and/or IF substantially free of R protein (prepared as in Example 1) was administered orally to mice. The IF was substantially free of R-protein and prepared as in Example 1. IF did not contain a detectable amount of R-protein using SDS PAGE electrophoresis technique.

Batch 1 (10 mice): 0.03 mg of IF alone per mouse

Batch 2 (10 mice): 0.03 mg of insulin per mouse

Batch 3 (10 mice): 0.03 mg of IF and insulin per mouse

Blood glucose level was measured with a blood glucose meter standard model Tracer (Boehringer) and produced the following results.

| Batch No. | t = 0 | 1 hour | 2 hours | 4 hours |
|---|---|---|---|---|
| 1: | 240 mg | 180 mg | 180 mg | 180 mg |
| 2: | 240 mg | 240 mg | 180 mg | 180 mg |
| 3: | 240 mg | 120 mg | 60 mg | 60 mg |

The greater decrease in blood glucose levels using IF and insulin as compared to IF or insulin alone is indicative of insulin being transported to the portal and/or lymphatic circulation system of the mice.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A method of delivering an insulin-containing composition to the circulation system of a host in need of insulin comprising:

administering orally to said host a pharmaceutical composition comprising:
  a) substantially pure intrinsic factor (IF),
  b) insulin, and
  c) a physiologically acceptable carrier, diluent, excipient or adjuvant;

wherein said composition is substantially free of R protein, wherein said IF is non covalently bound to said insulin, and wherein after oral administration, said insulin enters the circulation system.

2. The method according to claim 1, wherein said composition is substantially free of vitamin B12.

3. The method of claim 1 wherein said IF is produced using recombinant DNA techniques.

4. A pharmaceutical composition comprising substantially pure intrinsic factor(IF) non covalently bound to insulin, together with a physiologically acceptable carrier, diluent, excipient or adjuvant, wherein said composition is substantially free of R protein.

5. The composition of claim 3 wherein said IF is produced using recombinant DNA techniques.

6. The composition of claim 3 which is substantially free of Vitamin B12.

* * * * *